United States Patent [19]

Bornemann et al.

[11] Patent Number: 5,141,860

[45] Date of Patent: Aug. 25, 1992

[54] PREPARATION OF ACYLATED SUCROSE DERIVATIVES

[75] Inventors: Stephen Bornemann, Leamington Spa; John M. Cassells, St. Ives; Clive L. Combes, Reading, all of Great Britain; Jonathan S. Dordik, Iowa City, Iowa; Andrew J. Hacking, Mortimer, Great Britain

[73] Assignee: Tate & Lyle Public Limited Company, United Kingdom

[21] Appl. No.: 412,670

[22] Filed: Sep. 26, 1989

[30] Foreign Application Priority Data

Sep. 27, 1988 [GB] United Kingdom ............... 8822674

[51] Int. Cl.$^5$ .................... C12P 19/12; C12P 19/44
[52] U.S. Cl. .................... 435/100; 435/198; 435/72; 435/74
[58] Field of Search .................... 435/100, 198, 72, 74

[56] References Cited

U.S. PATENT DOCUMENTS

| 3,767,526 | 10/1973 | Suzuki et al. | 435/208 |
|---|---|---|---|
| 4,002,609 | 1/1977 | Khan | 536/119 |
| 4,362,869 | 12/1982 | Jenner et al. | 536/122 |
| 4,751,294 | 6/1988 | Jackson | 536/122 |

FOREIGN PATENT DOCUMENTS

| 357476 | 3/1990 | European Pat. Off. | 435/100 |
|---|---|---|---|
| 1437048 | 5/1976 | United Kingdom | 536/115 |
| 1492791 | 11/1977 | United Kingdom | 536/122 |
| 1543163 | 3/1979 | United Kingdom | |
| 2065648 | 7/1981 | United Kingdom | 536/115 |
| 2079749 | 1/1982 | United Kingdom | 536/115 |
| 2088855 | 6/1982 | United Kingdom | 536/122 |
| 2101989 | 1/1983 | United Kingdom | 536/115 |
| 2104063 | 3/1983 | United Kingdom | 536/122 |
| 2127807 | 4/1984 | United Kingdom | 536/122 |
| 2182039 | 5/1987 | United Kingdom | 536/122 |
| 2195632 | 4/1988 | United Kingdom | 536/115 |

OTHER PUBLICATIONS

Pu, *Chemical Abstracts*, vol. 112(9), May 7, 1990, #171972d.
Bai et al., *Biological Abstracts*, vol. 88(3), 1989, #29969.
Zheng et al., *Chemical Abstracts*, vol. 112(3), Jan. 15, 1990, #16029h.
Zhang et al., *Chemical Abstracts*, vol. 95(9), Aug. 31, 1991, #73690x.
Xia et al., *Chemical Abstracts*, vol. 113(25), Dec. 17, 1990, #224305t.
Hook Research Group, *Biological Abstracts*, vol. 79(9), 1985, #80151.
Chang, *Biological Abstracts*, vol. 79(10), 1985, #89135.
Li et al., *Biological Abstracts*, vol. 90(7), 1990, #79317.
Kirchner et al., *J. Am. Chem. Soc.* (1985), vol. 107, pp. 7072-7076.
Therisod et al., *J. Am. Chem. Soc.* (1986), vol. 108, pp. 5638-5640.
Zaks et al., *Science* (1984), vol. 224, pp. 1249-1251.

*Primary Examiner*—Ronald W. Griffin
*Assistant Examiner*—Pamela S. Webber
*Attorney, Agent, or Firm*—Ostrolenk, Faber, Gerb & Soffen

[57] ABSTRACT

Sucrose derivatives partially acylated in each ring can be obtained by treating a fully or partially acylated sucrose derivative with an enzyme having sucrose esterase activity capable of removing at least one acyl group from each ring, generally comprising or being a component of a lipase, esterase, amylase, α-galactosidase or protease preparation, the enzyme treatment being effected in an aqueous system. Sucralose can be obtained by using this method to obtain a sucrose 2,3,6,3',4'-penta ester which can then be chlorinated and de-esterfied. Some of the penta acetates, tetraacetates and mixed acetates/butyrates are new compounds.

22 Claims, No Drawings

PREPARATION OF ACYLATED SUCROSE DERIVATIVES

This invention relates to the preparation of partially acylated derivatives of sucrose by the enzymatic deacylation of sucrose octaacylates, particularly sucrose octaacetate (SOA), and to certain novel sucrose acylates prepared by this process.

Partially acylated sucrose derivatives are useful as intermediates in the preparation of other sucrose derivatives such as esters and ethers, in which the required substituents are at positions other than those protected by the acyl groups. These include certain intensely sweet derivatives of sucrose in which the hydroxy groups at one or more of the 4-, 1'-, 4'-, and 6'- positions are replaced by halogen atoms, as mentioned in British Patents No. 1,543,167; No. 2,088,855; No. 2,101,989; No. 2,104,063 and No. 2,127,806. Of particular interest amongst these compounds is the high intensity sweetener sucralose, 4,1',6'-trichloro-4,1',6'-trideoxygalactosucrose. Other compounds of interest that can be prepared by means of the acylated intermediates include sucrose benzoates, some of which posses useful bittering properties.

The synthesis of these compounds is complicated because of the selectivity that is required in the substitution of particular hydroxyl groups. It is necessary to protect at least some of the hydroxyl groups that are to be retained while some or all of the other hydroxyl groups are replaced with the desired substituents.

One method of achieving this is described in British Patent No. 2,065,648B which relates to the preparation of sucralose. It involves reacting the 6-, 1'- and 6'- positions of sucrose with trityl chloride and reacting the remaining free hydroxyl groups with acetic anhydride, followed by removing the trityl groups. The acetate group at position 4 may be migrated to the 6- position and the resulting compound with only the 4,1'- and 6'-hydroxyl groups free may be chlorinated and the acetate groups removed to yield sucralose. Alternatively the greater reactivity of the 4-, 6-, 1'- and 6'- positions may be exploited. If one or more of these positions is protected then the remainder may be selectively chlorinated using milder reaction conditions. Thus in British Patents 2,079,749 and 2,195,632 the 6-position is acetylated, the 4-, 1'- and 6'- positions are chlorinated and the acetate is removed to give sucralose.

A strategy that has more general applicability and could yield a range of halogenated sucrose derivatives involves the selective removal of acyl groups from octaacyl derivatives of sucrose. One such compound is sucrose octaacetate which can be synthesized cheaply from sucrose and acetic anhydride and is available commercially.

Selective chemical de-esterification of SOA is limited to only a few positions. Thus Ballard, Hough and Richardson (Carbohydrate Research 24, 152, 1972 and 34, 184, 1974) obtained a mixture of hepta-O-acetyl sucroses (OH 6 or 6' or 4') by deacylation of sucrose octaacetate (SOA) in chloroform on an aluminum oxide column. Later, Capek, Vydra, Ranny and Sedmera (Collection Czechoslovak Chem. Commun. 50, 2191, 1985) obtained in addition to the heptaacetates, two hexaacetates (OH 1' and 3', OH 3' and 4') by deacetylation of a methanolic solution of SOA on aluminum oxide impregnated by potassium carbonate. Recently Haines, Konowicz and Jones obtained the 2,3,4,6,1',6'-hexa acetate by storing SOA in n-propylamine at room temperature for 50 minutes or in isopropylamine at room temperature for 72 hours (personal communication). Thus, very few of the intermediates required for the production of sweet chlorosugars can be prepared by chemical deacylation of SOA. Acetyl groups can be removed from one ring of sucrose (6- or 6'-, or 4'-, or 1'- and 3'-, or 3'- and 4'-) but not from both.

Another possibility is to achieve this specificity using enzymatic catalysis. Several groups of enzyme will catalyse de-acylation reactions although all come in the general classification of hydrolytic enzymes. Esterases predominantly hydrolyse glycerol esters, but will act on a wide range of substrates. Lipases are a class of esterases which work at interfaces, which in nature usually means membranes, but they will work at the interface of two immiscible liquids. Proteases will also hydrolyze esters. There are several classes: serine, sulphydryl and metaloproteinases, for example, all of which can show de-esterification activity. As a sugar is being used in this work, it may be speculated that carbohydrase enzymes which normally hydrolyze the bond between two sugar moieties might hydrolyze a sugar ester.

A further possibility is to combine chemical and enzymatic methods to deacylate sucrose octaacylates prepared by chemical deacylation may be further treated with an enzyme to effect hydrolysis of additional acyl groups.

Nearly all the published work in this areas has concerned the selective deacylation of monosaccharides. Thus, for example, H. M. Sweers and C-H Wong (J Am Chem Soc 1986, 108, 6421-6422) have reported the regioselective deacylation of methyl 2,3,4,6-tetra-O-pentanoyl-D-hexopyranosides to give the 6-hydroxy derivatives, using the lipase from *Candida cylindracea*. The reaction was carried out in phosphate buffer (0.1M, pH 7) at ambient temperature, with stirring, over three days, the substrate being added as a solution in acetone. Deacylation was specific to the 6-position. Acetyl derivatives were not substrates for the enzyme.

The only report known to us of enzymatic deacylation of an acylated disaccharide substrate was described by Kloosterman et al at a meeting in Stockholm in August 1988. They showed that wheat germ lipase (Sigma L-3001) under aqueous conditions removed three acetyl groups from sucrose octaacetate, all from the fructose ring; thus obtaining the 1', 4', 6'-tri-hydroxy pentaacetate.

There is thus a need for a method of removing selected acyl groups from both rings of sucrose octaacetate (SOA).

SOA is insoluble in water and therefore would not seem to be an easy subject for deacylation by enzymatic hydrolysis. However, we have found that certain lipase, protease and esterase enzymes can be used to deacylate SOA in certain organic solvents in the presence of water, generally 50% or more, or in aqueous dispersions of SOA. Further, these enzymes can be used to deacylate SOA selectively, at one or more of the 4-, 6-, 1'-, 4' and 6'- positions, leaving at least the 2-, 3- and 3'- positions protected.

Thus, according to the present invention we provide a method for the preparation of tri-, tetra-, penta-, hexa- or heptaacylates of sucrose with acyl groups at least the 2-, 3- and 3'- positions and, where there are two or more hydroxy groups present at least one hydroxy group on the glucose ring by enzymatic hydrolysis of sucrose octaacylates.

Water miscible solvents such as acetone may be used, or the reaction can be carried out in a biphasic system of water and a solvent which is immiscible or only slightly miscible with water, such as toluene or xylene. In such biphasic systems SOA remains in the solvent phase, the enzyme is found in the aqueous phase and at the interface between the phases, and the products partition into the aqueous phase.

The enzymes that can be used in the process of the present invention are lipases and esterases, many of which are available commercially and are used to hydrolyse fats and oils to produce fatty acids and glycerol or to deesterify various esterified compounds. Other types of enzyme that may be used include amylases, and α-galactosidases.

Some of these enzymes are available as fairly crude enzyme preparations which may also contain other types of enzyme, such as proteases. Similarly, other enzyme preparations with principal activity against substances other than lipids and esterified compounds, may also contain lipases or esterases that can be used to deacylate sucrose octaacylates. Thus we have found certain 'proteases' that can be used to deacylate SOA.

We have found that different enzymes will remove different combinations of acyl groups from sucrose octaacylates. Indeed, some enzymes will remove some acyl groups under certain conditions and additional ones under more forcing conditions.

For example, the following enzymes can be used to prepare the following sucrose 2,3,3'- acetates from sucrose octaacetate:

| Enzyme | 4 | 6 | 1' | 4' | 6' |
|---|---|---|---|---|---|
| α-galactosidase (Stachyase, Amano Chem. Corp) | OH | OAc | OAc | OAc | OAc |
| Fungal α-amylase (Rapidase RP, Miles Labs) | OH | OAc | OAc | OAc | OH |
| α-galactosidase (Melibiase Hokkaido Sugar Co) | OH | OAc | OAc | OH | OH |
| | plus OH | OH | OAc | OAc | OH |
| Aspergillus melleus protease A 10,000 (Tanabe Seiyaku Co) | OH | OH | OAc | OAc | OH |
| Yeast esterase (Glaxo Ltd) | OH | OAc | OH | OH | OH |
| | (plus OAc | OH | OH | OH | OH) |
| | and OH | OAc | OH | OH | OAc |
| | (plus OAc | OH | OH | OH | OAc) |
| Pancrelipase (Scientific Protein Laboratories) | OAc | OAc | OAc | OH | OAc |
| Subtilisin Carlsberg (Alcalase 2.OT, Novo Enzyme Products Ltd) | OAc | OAc | OH | OAc | OAc |
| | (plus OAc | OAc | OH | OAc | OH) |
| | (plus OH | OAc | OH | OAc | OH) |
| Subtilisin Carlsberg (Sigma Chemical Co) | OAc | OAc | OH | OAc | OAc |

Is, of course, possible to use a combination of enzymes, either simultaneously or sequentially, to obtain the desired combination of free hydroxy groups.

Thus a sucrose heptaacetate obtained by treatment of SOA with one enzyme may be treated with another to provide hexa, penta, tetra- or tri-acetates. Similarly, a hexaacetate obtained with one enzyme may be treated with another to produce penta-, tetra-, or tri-acetates.

Also, as mentioned above, the hepta- or hexa acetates obtained by chemical deacylation of SOA (or even by direct synthesis from sucrose, e.g. British Patents 1,492,791 and 1,437,048) may be further treated with an enzyme to produce the desired hexa-, penta-, tetra- and triacetates.

We have also found that certain enzymes are much more reactive to lower acyl groups, such as acetyl groups, than to somewhat higher acyl groups such as butyryl groups. This leads to a particular embodiment of the present invention in which treatment of SOA with pancreatic lipase to remove 4'-acetyl is followed by butyrylation of the 4'-hydroxy group by treatment with, say, butyric anhydride. This is then followed by treatment with yeast esterase. Acetyl groups in the 4-, 1'- and 6'-positions are removed, but the 4'-butyryl group remains to provide a 4'-butyryl analogue of sucrose 2,3,6,3',4'-pentaacetate (6-PAS), a key intermediate in the preparation of sucralose. Similar results may be obtained by chemical deacylation of SOA to remove the 4'-acetyl group or the 3'- and 4'-acetyl groups, followed by butyrylation or the deprotected hydroxyl groups and then by treatment with yeast esterase to provide a 4'-butyryl or a 3',4'-dibutyryl analogue of 6-PAS.

Another factor that can be important in the enzymatic deacylation of sucrose acylates is migration of the acyl groups from acylated to de-acylated positions during the reaction. Thus, some enzymes, such as the Subtilisins, are most effective under alkaline conditions (pH 7 and above) under which migration of acetyl groups from the 4- position to the 6- position occurs fairly readily and migration from 3- to 4- and 2- to 3- occurs more slowly. Thus it may be possible to maximise the yield of a particular acylate by shortening or by prolonging the reaction time or by careful control of the pH of the reaction. This factor is less important for enzymes which are most effective at a pH of about 5, but operation at a higher or lower pH tends to promote migration.

We also provide the use of sucrose acylates prepared by the method of the present invention in the preparation of halogenated sucrose derivatives, especially sucralose. Thus, 6-PAS or its 4'-butyryl or its 3',4'-dibutyryl analogues can be chlorinated at the 4'-, 1'- and 6'-positions, followed by removal of the acyl groups to provide sucralose. Chlorination of these intermediates prepared by the method of the present invention can be effected by various methods disclosed in GB 2,065,648B and GB 2,182,039 or in our co-pending British Patent Application No. 8917468.4. Similarly, 2,3,4,3'-tetra-O-acetyl sucrose can be chlorination and then deacetylated to provide the intensely sweet 4,1',4',6'-tetrachloro-4,1',4',6'-tetradeoxy galactosucrose disclosed in GB 2,088,855.

Several of the sucrose acylates prepared according to the above-described method are novel compounds and constitute a further feature of the invention, namely:

| | |
|---|---|
| 2,3,6,1',3'-penta-O-acetyl sucrose | (OH at 4,4',6') |
| 2,3,1',3',4'-penta-O-acetyl sucrose | (OH at 4,6,6') |
| 2,3,6,3',6'-penta-O-acetyl sucrose | (OH at 4,1',4') |
| 2,3,4,3',6'-penta-O-acetyl sucrose | (OH at 6,1',4') |
| 2,3,6,3'-tetra-O-acetyl sucrose | (OH at 4,1',4',6') |
| 2,3,4,3'-tetra-O-acetyl sucrose | (OH at 6,1',4',6') |
| 2,3,6,3'-tetra-O-acetyl-4'-O-butyryl sucrose | (OH at 4,1',6') |
| 2,3,4,6,1',3',6'-hepta-O-acetyl-4'-O- | |

| butyryl sucrose | (no OH) |
|---|---|

The $^1$H-NMR spectra of these compounds are listed below.

The $^1$H-n.m.r. spectra were recorded after deuterioacetylation (by the method of T. Sumai et al., *Bull. Chem. Soc. Japan*, 43 (1970) page 1219) to allow unambiguous characterisation of the number and position of the acetate groups in the partially acetylated sucrose derivatives.

2,3,6,1′,3′-Penta-O-acetylsucrose

The $^1$H-n.m.r. spectrum ($C_5D_5N:C_6D_6$, 1:1; 250 MHz) revealed signals at $\delta$1.94, 1.90, 1.89, 1.81 and 1.78 due to acetate groups at C-3′,2,6,1′ and 3, respectively, which confirmed that the three hydroxyl groups were located at C-4,4′,6′.

2,3,1′,3′,4′-Penta-O-acetylsucrose $^1$H-n.m.r. spectrum (deuterioacetylation) ($C_5D_5N:C_6D_6$, 1:1; 250 MHz) revealed five signals at $\delta$1.93, 1.89, 1.80, 1.77, 171, due to acetate groups at C-3′,2,1′,3 and 4′ respectively.

2,3,4,3′,6′-Penta-O-acetylsucrose

The deuterioacetylated $^1$H-n.m.r. spectrum (same conditions as above) showed five signals at $\delta$1.94, 1.90, 1.83, 1.79 and 1.76 due to the acetate protons at C-3′,2,6′,3 and 4, respectively, confirming the structure of the above sucrose pentaacetate.

2,3,6,3′-Tetra-O-acetylsucrose $^1$H-N/m/r (CDCl$_3$, 250 MHz: $\delta$5.53 (d, 1H, $J_{1,2}$ 3.5 Hz, H-1); 4.76 (dd, 1H, $J_{2,3}$ 10.0 Hz, H-2); 5.27 (t, 1H, $J_{3,4}$ 10.0 Hz, H-3), 5.22 (d, 1H, $J_{3,4'}$ 7.7 Hz, H-3′); 4.45–4.27 (m, 2H, H-6a, H-6b); 2.19, 2.11, 2.08, 2.04 (4S, 12H, 4 acetates).

The four acetate signals at 2,3,6 and 3′ positions were further confirmed by deuterioacetylation followed by $^1$H-n.m.r. of the acetate resonances ($C_5D_5N:C_6D_6$, 1:1; 250 MHz): $\delta$1.94 (3′-Ac) 1.90 (2-Ac); 1.89 (6-Ac); 1.79 (3-Ac).

2,3,4,3′-Tetra-O-acetylsucrose $^1$H-N.m.r. (CDCl$_3$, 250 MHz): $\delta$5.62 (d, 1H, $J_{1,2}$ 3.5 Hz, H-1); 4.80 (dd, 1H, $J_{2,3}$ 10.0 Hz, H-2); 5.41 (t, 1H, $J_{3,4}$ 10.0 Hz, H-3); 4.89 (t, 1H, $J_{4,5}$ 10.0 Hz, H-4); 5.20 (d, 1H, $J_{3',4'}$ 7.5 Hz, H-3′); 1.99, 2.04, 2.15, 2.20 (4S, 12H, 4 acetates). The four acetate resonances at 2,3,4 and 3′ were further confirmed by deuterioacetylation of the tetraacetate followed by H$^1$-n.m.r of the acetate signals ($C_5D_5N$: $C_6D_6$, 1:1, 250 MHz): $\delta$1.94 (3′-Ac); 1.90 (2-Ac); 1.79 (3-Ac); 1.76 (H-Ac).

2,3,6,3′-Tetra-O-acetyl-4′-O-butyrylsucrose $^1$H-N.m.r. (CDCl$_3$, 250 MHz): $\delta$5.58, (d, 1H, $J_{1,2}$ 3.6 Hz); 4.82 (dd, 1H, $J_{2,3}$ 10.3 Hz, H-2); 5.27 (t, 1H, $J_{3,4}$ 10.1, H-3) 5.43 (d, 1H, $J_{3',4'}$, 3.2 Hz, H-3′); 4.29–4.53 (2 dd, 2H, H-6a, H6b); 3.26 (d, 1H, J, 5.2 Hz, 10H); 2.95 (t, 1H, J 6.4 Hz, 10H); 2.66 (t, 1H, J 6.8 Hz, 10H); 2.30 (t, 2H, J, 7.2.Hz, CH$_2$); 1.62 (dd, 2H, J, 7.4 Hz, CH$_2$); 0.92 (t, 3H, J 7.4 Hz, CH$_3$). The four acetate signals were further confirmed by deuterioacetylation followed by $^1$H-n.m.r. of the acetate signals ($C_5D_5N$: $C_6D_6$, 1:1; 250 MHz, $\delta$1.94 (3′-Ac); 1.90 (2-Ac); 1.88 (6-Ac); 1.78 (3-Ac).

2,3,4,6,1′,3′,6′-Hepta-O-acetyl-4′-O-butyrylsucrose $^1$H-N.m.r. (CDCl$_3$, 250 MHz): $\delta$6.25 (d, 1H, $J_{1,2}$ 3.5 Hz); 5.42 (dd, 1H, $J_{2,3}$ 10.5 Hz, H-2); 6.11 (t, 1H, $J_{3,4}$ 10.1 Hz, H-3); 5.66 (t, 1H, $J_{4,5}$, 5.9 Hz, H-4′); 2.26, 2.22, 2.20, 2.10 (4S, 21 $^1$H$^1$, 7Ac); 2.39 (t, 2H, J 7.1 Hz CH$_2$) 1.72 (dd, 2H, J 7.2 Hz, CH$_2$); 0.98 (t, 3H, J 7.3 Hz, CH$_3$).

The following Examples illustrate the invention:

EXAMPLE 1

Preparation of 2,3,6,1′,3′,4′,6′-hepta-O-acetyl sucrose

A reaction mixture of sucrose octaacetate (10 g), alpha-galactosidase (Stachyase, Amano Chem. Corp.: 2.5 g) and acetone 10% (v/v) in 1 liter phosphate buffer (100 mM pH 7.0) was incubated with stirring at 30° C. for 72 h. The reaction mixture was then extracted with an equal volume of ethyl acetate, evaporated to dryness, mixed with silica gel (40 g) and applied to a column containing 160 g silica gel. After elution with diethyl ether: petrol=4:1 (1 liter) and diethyl ether (1 liter), fractions were collected and analysed for sucrose acetates. A yield of 2.2 g 2,3,6,1′,3′,4′,6′-hepta-O-acetyl sucrose was obtained, from the diethyl ether fractions.

EXAMPLE 2

Preparation of 2,3,4,6,3′,4′,6′-hepta-O-acetyl sucrose

A reaction mixture containing sucrose octaacetate (7 g), 500 mg Subtilisin Carlsberg (Sigma Chemical Co.) and acetone (30% v/v) in 250 ml phosphate buffer (100 mM pH 7.0) was incubated with stirring at 30° C. for 72 h. The reaction mixture was extracted with an equal volume of ethyl acetate and evaporated to dryness under vacuum. The solid residue (6.5 g) was mixed with silica gel and applied to a silica column (200 g) which was eluted with (1) diethyl ether: petrol, 4:1 and (2) diethyl ether. A heptaacetate identified as the 2,3,4,6,3′,4′,6′ was obtained from diethyl ether fractions. The yield was 2.9 g.

EXAMPLE 3

Synthesis of 2,3,6,1′,3′,4′-hexa-O-acetyl sucrose

A suspension of sucrose octaacetate (14 g) in 2 liters citrate phosphate buffer (100 mM pH 5.0) and 10 g commercial crude fungal alpha amylase preparation (Rapidase RP, Miles Laboratories) was incubated with stirring at 30° C. for 168 h. The mixture was then treated with Amberlite XAD-4 resin (BDH Chemicals, Poole, England) to adsorb all sucrose esters. The resin was recovered by filtration, loaded into a glass column and eluted with acetone (1 liter). The material recovered (6.0 g) was dissolved in a small volume of methanol mixed with silica gel (20 g) and evaporated to dryness under vacuum at 50° C. This mixture was added to a silica column (132 g) and eluted sequentially with diethylether (1 liter), diethyl ether:acetone 5:1 (900 ml), diethyl ether:acetone=4:1 (1 liter). Fractions of each eluate were examined by gradient HPLC and GC for their sucrose ester content. The 2,3,6,1′,3′,4′ hexa-O-acetyl sucrose (300 mg) was obtained from a diethylether:acetone (4:1) fraction and its identity confirmed by proton NMR analysis after deuteroacetylation.

EXAMPLE 4

Synthesis of 2,3,6,1′,3′-penta-O-acetyl sucrose

A suspension of sucrose octacetate (20 g) and an alpha galactosidase (Melibiase, Hokkaido Sugar Company) in 4 liters citrate-phosphate buffer (100 mM pH 5.0) was incubated with stirring at 30° C. for 120 h. The mixture was extracted twice with an equal volume of ethyl acetate and after evaporation of the solvent under vacuum. 11.2 g of a mixture of sucrose acetates was obtained. This mixture was separated using silica gel chromatography with ethyl acetate:petroleum ether (9:1, v/v) as eluant. Fractions containing 2,3,6,1',3' penta-O-acetyl sucrose (950 mg) were pooled and evaporated to dryness.

EXAMPLE 5

Synthesis of 2,3,1',3',4'-penta-O-acetyl sucrose

Fractions of the eluate of the silica column in Example 4 were also found to contain sucrose 2,3,1',3',4' penta-O-acetyl sucrose and when pooled and evaporated to dryness 700 mg of pure product was obtained.

As an alternative, a reaction mixture containing 7 g of sucrose octaacetate and 5 g *Aspergillus melleus* protease (A 10,000- Tanabe Seiyaku Co. Japan) was incubated with stirring in 1 liter citrate phosphate buffer (100 mM pH 5.0) for 65 h. at 30° C. The mixture was then extracted with 3 equal volumes of ethyl acetate and after pooling the extracts and evaporating to dryness, 6.3 g of a syrup containing a mixture of sucrose acetates was obtained. The mixture was resolved by silica gel chromatography using diethyl ether:acetone (5:0. v/v) as eluant. Fractions containing 150 mg of pure 2,3,1',3',4' penta-O-acetyl sucrose were pooled and evaporated to dryness.

EXAMPLE 6

Synthesis of 2,3,6,3' tetra-O-acetyl sucrose and 2,3,4,3'-tetra-O-acetyl sucrose A reaction mixture containing sucrose octaacetate (3.5 g) and yeast esterase (Glaxo Ltd., 3.0 g) in 500 ml citrate-phosphate buffer (100 mM, pH 5.0) was incubated with stirring at 30° C. for 50 h. The mixture was extracted twice with equal volumes of ethyl acetate and 2.6 g of a mixture of sucrose acetates was obtained. The mixture was resolved using a silica gel column eluted by ethyl acetate. Fractions containing sucrose 2,3,6,3' tetra-O-acetyl sucrose (100 mg) and sucrose 2,3,4,3' tetra-O-acetyl sucrose (320 mg) were obtained. The 2,3,4,3' product could be converted into the 2,3,6,3' isomer by acetyl migration from the 4- to 6- position through incubation in Tris HCl buffer (100 mM pH 8.0) for 5 h. at 30° C.

EXAMPLE 7

Synthesis of 2,3,6,3'-tetra-O-acetyl sucrose and 2,3,4,3'-tetra-O-acetylsucrose in a biphasic system (water and xylene)

A reaction mixture comprising sucrose octaacetate (100 g), yeast esterase (Glaxo Ltd., 30 g), xylene (1 liter) and 1 liter citrate phosphate buffer (100 mM, pH 5.0) was incubated with stirring at room temperature for 72 h. After this time 800 ml of the aqueous phase was removed and extracted twice with equal volumes of ethyl acetate. The solvent extractions were pooled, evaporated to dryness and the mixed sucrose acetates (6 g) separated by silica gel chromatography using ethyl acetate:acetone=9:1 (v/v) then 2.3 liters ethyl acetate:acetone=8:2 (v/v). Yields of 900 mg 2,3,4,3'-tetra-O-acetyl sucrose and 300 mg of 2,3,6,3'-tetra-O-acetyl sucrose were obtained. The 2,3,4,3'-tetraacetate was converted into its 2,3,6,3'-isomer by migration of the acetate from the 4 to the 6 position, as described above in Example 6.

EXAMPLE 8

Preparation of 2,3,6,3',6'-penta-O-acetyl sucrose and 2,3,4,3',6'-penta-O-acetyl sucrose It also proved possible to isolate the 2,3,6,3',6' and 2,3,4,3',6' penta-O-acetyl sucroses (using the yeast esterase) by the procedure of Example 7 by reducing the reaction time to about 60 h. In one run 8 g of mixed sucrose acetates were obtained and then separated by silica gel chromatography using 2 liters ethyl acetate-:acetone (8:2 (v/v)), to provide 80 mg of a mixture of these two pentaacetates. Again, the 2,3,6,3',6'- product was obtained from the 2,3,4,3',6'-ester by migration of the acetate from the 4 to the 6 position, as described in Example 6.

EXAMPLE 9

Preparation of 2,3,6,3'-tetra-O-acetyl-4'-O-butyrylsucrose

A reaction mixture of sucrose octaacetate (12.6 g) and Pancrelipase (Scientific Protein Laboratories, 10 g) in 2 liters citrate-phosphate buffer (100 mM, pH 5.0) was incubated with stirring at room temperature for 22 h. The solution was filtered, the filtrate was extracted with ethyl acetate (6×1 liter) and the extract was concentrated to a syrup. The syrup was loaded onto a silica gel column and eluted with diethyl ether (2 liters). A yield of 7.5 g of the 2,3,4,6,1',3',6'-hepta-O-acetyl sucrose was obtained from the column.

A solution of 2,3,4,6,1',3',6' hepta-O-acetyl sucrose (7.5 g) in pyridine (20 ml) was incubated with butyric anhydride (6 ml) at room temperature for 24 h. The solution was diluted with methanol (50 ml) at 40° C., concentrated to a syrup and re-dissolved in methylene chloride (50 ml). This solution was washed with aqueous sodium hydrogen carbonate, the organic layer was dried with $Na_2SO_4$ and evaporated to give 7.6 g of the 4'-butyrate sucrose heptaacetate.

A suspension of 4'-butyrate sucrose heptaacetate (7.6 g) and acetone (50 ml) in 1 liter citrate-phosphate buffer (100 mM, pH 5.0) was incubated with yeast esterase (10 g) at room temperature for 34 h. The reaction mixture was extracted with ethyl acetate (2×1 liter) and the extract was concentrated to give a mixture of esters. This mixture was treated with glacial acetic acid (1% v/v) in toluene (16.5 ml) at 90°-20° C. for 6 h to effect migration of 4-acetyl groups to the 6 position. The solution was concentrated, applied to a silica gel column and eluted using ethyl acetate-petrol (3:2 v/v) to give the 2,3,6,3'-tetra-O-acetyl-4'-O-butyrylsucrose (1.45 g).

EXAMPLE 10

Preparation of 2,3,6,3',4' penta-O-acetyl sucrose (6-PAS)

A reaction mixture of sucrose octaacetate (10 g) and Subtilisin Carlsberg (Alcalase 2.0T, Novo Enzyme Products Ltd, 75 g) in 1 liter phosphate buffer (200 mM, pH 7.0) was incubated with stirring at 45° C. for 24 h. The pH was maintained at 7.0 by addition of sodium hydroxide. The reaction mixture was filtered, the filtrate extracted with ethyl acetate (2×1 liter) and the organic phase dried with $Na_2SO_4$ and evaporated to a syrup. The syrup was applied to a silica gel column and sequentially eluted with ethyl acetate-petrol (1:1 v/v, 1 liter), (3:2 v/v, 500 ml), (17:3 v/v, 1 liter) and ethyl acetate (1 liter). A pentaacetate fraction (0.74 g) was obtained which contained 36% 2,3,6,3',4' penta-O-acetyl sucrose, as determined by gas chromatography analysis.

This compound was extracted and crystallized from this mixture using hot methylated spirit. A yield of 0.16 g 6-PAS was obtained.

EXAMPLE 11

Preparation of 6-PAS

A hexaacetate fraction was also isolated from the silica gel column in Example 10. This fraction, comprising 50% by weight 2,3,4,6,3',4'-hexa-O-acetyl sucrose, was isolated from the mixture at 99% purity by crystallization from hot methylated spirit.

A reaction mixture containing the 2,3,4,6,3',4'-hexacetate (25 mg), Stachyase (Amano Chemical Corp 10 mg), acetone (0.4 ml), NaCl (200 mM) and $CaCl_2$ (3 mM) in 4 ml phosphate buffer (100 mM, pH 7.0) was incubated with stirring at 30° C. for 24 h. The reaction mixture was extracted with ethyl acetate (2×2 ml) and the organic phase was evaporated to a syrup (20 mg) containing 40% 6-PAS as determined by gas chromatography.

EXAMPLE 12

Preparation of 4,1',6'-trichloro-4,1',6'-trideoxygalactosucrose (sucralose)

A suspension of 2,3,6,3'-tetra-O-acetyl-4'-O-butyryl-sucrose prepared by the method of Example 9 (1.5 g) and triphenyl phosphine oxide (0.75 g) in toluene (7) was treated with thionyl chloride (0.8 ml) initially at 0° C. and then at 95° C. for 16 h. The reaction mixture was diluted with ethyl acetate (10 ml), washed with aqueous sodium carbonate followed by water, dried over $Na_2SO_4$ and concentrated to a syrup. The syrup was purified on a silica gel column, eluted by diethyl ether-petrol (3:1 v/v), to provide 1.2 g of the 4,1',6' trichloro-4'-butyryl-sucrose tetraacetate as a syrup. A solution of the syrup (1 g) in dry methanol (6 ml), was treated with M sodium methoxide (pH 10.0) at room temperature for 4 h. The solution was neutralized with Amberlyst 15 resin (H+ form), concentrated to a syrup and redissolved in ethyl acetate. Sucralose crystallized from the solution in a yield of 0.57 g.

EXAMPLE 13

Preparation of Sucralose (a) 2,3,4,6,1',6'-hexa-O-acetyl sucrose

A solution of sucrose octaacetate (20 g) in n-propylamine (200 ml) was stored at room temperature for 50 minutes and then concentrated to a residue under reduced pressure. The residue was subjected to column chromatography on silica gel with ethyl acetate-diethyl ether (7:4) as eluant and the major component (Rf 0.3) comprising 2,3,4,6,1',6'-hexa-O-acetyl sucrose (3.82 g) was isolated.

(b) 3',4'-di-O-butyryl-2,3,4,6,1',6'-hexa-O-acetyl sucrose

A solution of 2,3,4,6,1',6'-hexa-O-acetyl sucrose (3.82 g) in pyridine (12 ml) was incubated with butyric anhydride (6 ml) at room temperature for 24 h. The solution was diluted with methanol (30 ml) at 40° C., concentrated to a syrup and then redissolved in methylene chloride (30 ml). This solution was washed with aqueous sodium hydrogen carbonate and the organic layer was then dired with $Na_2SO_4$ and evaporated to give 3.91 g of the 3'4'-di-O-butyryl sucrose hexaacetate.

(c) 2,3,6-tri-O-acetyl-3',4'-di-O-butyryl sucrose

A suspension of the 3',4'-di-O-butyryl sucrose hexaacetate (3.91 g) and acetone (30 ml) in 600 ml citrate-phosphate buffer (100 mM, pH 5.0) was incubated with yeast esterase (6 g) at room temperature for 40 h. The reaction mixture was then extracted with ethyl acetate (2×600 ml) and the extract was concentrated to a solid residue. The residue was treated with glacial acetic acid (1% w/v) in toluene (10 ml) at 95° C. for 6 h to cause migration of the 4-acetyl groups to the 6-position. The solution was then concentrated, loaded onto a silica gel column and eluted with ethyl acetate-petrol (3:2 v/v) to isolate 2,3,6-tri-O-acetyl-3'-4'-di-O-butyryl sucrose (0.73 g).

(d) Sucralose

A suspension of 2,3,6-tri-O-acetyl-3',4'-di-O-butyryl sucrose (0.73 g) and triphenylphosphine oxide (0.36 g) in toluene (3.5 ml) was treated with thionyl chloride (0.40 ml) initially at 0° C. and then at 95° C. for 16 h. The reaction mixture was worked up as described in Example 12 to provide 0.24 g sucralose.

EXAMPLE 14

Preparation of Sucralose (a) Sucralose pentaacetate (TOSPA)

6-PAS prepared by the method of Example 10 (3.2 g) was slurried in toluene (8 ml) and benzyltriethylammonium chloride (0.4 g) was added. Thionyl chloride (1.7 ml) was then added and the reaction mixture was maintained at ambient temperature for 30 minutes and then heated to 105° C. and held at reflux for 3 hours. The reaction mixture was cooled to 30° C. and water (2.0 ml) was added. After cooling for 30 minutes at 15°–20° C. the produce was collected by filtration, washed with toluene (5 ml) and water (5 ml) and dried in vacuo at 40° C., Yield 3.5 g; 82.1% TOSPA; molar yield 85%.

(b) Sucralose

TOSPA (3.5 g) was taken up in methanol (10 ml) and sodium methoxide (0.04 g) was added. The mixture was incubated at room temperature for 1.5 hours under vacuum. The resulting solution was neutralised by stirring with Amberlite IRC 50 (H+) resin (0.5 g) and then the resin was removed by filtration and washed with methanol (5 ml). The filtrate and wash were stirred with decolourising charcoal (0.2 g) and celite (0.2 g) for 15 minutes, then the solution was clarified by filtration and concentrated to a froth in vacuo. Crystalline sucralose was isolated by taking up the froth in ethyl acetate (20 ml), filtering, washing with ethyl acetate (5 ml) and drying in vacuo at 40° C. Yield 1.86 g (94%).

We claim:

1. A method for the preparation of partly deacylated acylate of sucrose having acyl groups at least at the 2-, 3-, and 3'- positions and at least one free hydroxyl group in each ring, in which a sucrose octaacylate is treated with an enzyme or combination of enzymes capable of catalyzing the hydrolysis of at least one acyl group from each ring of said sucrose octaacylate in an aqueous medium comprising water and up to 50% organic solvent buffered to a pH of 5–7, and isolating the resulting partly deacylated sucrose acylate, said enzymes being selected from the group consisting of pancreatic lipases, yeast esterase, fungal α-amylases, subtilisins, Aspergillus melleus protease and α-galactosidases.

2. The method of claim 1, wherein said enzyme or combination of enzymes comprises α-galactosidase (stachyase), whereby 2, 3, 6, 3′, 4′-penta-O-acetyl sucrose is formed from 2, 3, 4, 6, 3′, 4′-hexa-O-acetyl sucrose.

3. The method of claim 1, wherein said enzyme or combination of enzymes comprises yeast esterase and 2, 3, 6, 3′-tetra-O-acetyl-4′-O-butyryl sucrose is formed from 2, 3, 4, 6, 1′, 3′, 6′-hepta-O-acetyl-4′-O-butyryl sucrose.

4. The method of claim 1, wherein said enzyme or combination of enzymes comprises yeast esterase, and 2, 3, 6-tri-O-acetyl-3′, 4′-di-O-butyryl sucrose is formed from 2, 3, 4, 6, 1′, 6′-hexa-O-acetyl-3′, 4′-di-O-butyryl sucrose.

5. The method of claim 3 in which said sucrose octaacylate is prepared by treating sucrose octaacetate with pancreatic lipase to obtain the 2, 3, 4, 6, 1′, 3′, 6′-heptaacetate which is then butyrylated at the 4′- position.

6. The method of claim 1 wherein said enzyme or combination of enzymes comprises an α-galactosidase, whereby a 4-acyl group is removed.

7. The method of claim 1 wherein said enzyme or combination of enzymes comprises subtilisin Carlsberg, whereby a 1′- acyl group is removed either alone or together with acyl groups in the 4- and 6′- positions.

8. The method of claim 1 wherein said enzyme or combination of enzymes comprises a fungal α-amylase, whereby acyl groups in the 4- and 6′- positions are removed.

9. The method of claim 1 wherein said enzyme or combination of enzymes comprises yeast esterase whereby acyl groups from the 4-, 1′- and 6′- positions are removed.

10. The method of claim 1 wherein said sucrose octaacylate is sucrose octaacetate and said enzyme or combination of enzymes comprises α-galactosidase (stachyase) whereby 2, 3, 6, 1′, 3′, 4′, 6′, - hepta-O-acetyl sucrose is formed.

11. The method of claim 1 wherein said sucrose octaacylate is sucrose octaacetate and said enzyme or combination of enzymes comprises subtilisin Carlsberg whereby 2, 3, 4, 6, 3′, 4′, 6′-hepta-O-acetyl sucrose is formed.

12. The method of claim 1, wherein said sucrose octaacylate is sucrose octaacetate and said enzyme or combination of enzymes comprises fungal α-amylase, whereby 2, 3, 6, 1′, 3′, 4′-hexa-O-acetyl sucrose is formed.

13. The method of claim 1, wherein said sucrose octaacylate is sucrose octaacetate and said enzyme is α-galactosidase (melibiase), whereby a member of the group consisting of 2, 3, 6, 1′, 3′-penta-O-acetyl sucrose and 2, 3, 1′, 3′, 4′-penta-O-acetyl sucrose is formed.

14. The method of claim 1, wherein said sucrose octaacylate is sucrose octaacetate and said enzyme comprises aspergillus melleus protease and 2, 3, 1′, 3′, 4′-penta-O-acetyl sucrose is formed.

15. The method of claim 1, wherein said sucrose octaacylate is sucrose octaacetate and said enzyme comprises yeast esterase whereby a member of the group consisting of 2, 3, 6, 3′, 6′-penta-O-acetyl sucrose, 2, 3, 4, 3′, 6′-penta-O-acetyl sucrose, 2, 3, 6, 3′-tetra-O-acetyl sucrose and 2, 3, 4, 3′-tetra-O-acetyl sucrose is formed.

16. The method of claim 1, wherein said sucrose octaacylate is sucrose octaacetate and said enzyme comprises pancreatic lipase, whereby 2, 3, 4, 6, 1′, 3′, 6′-hepta-O-acetyl sucrose is formed.

17. The method of claim 1, wherein said sucrose octaacylate is sucrose octaacetate and said enzyme is subtilisin Carlsberg, whereby 2, 3, 6, 3′, 4′-penta-O-acetyl sucrose is formed.

18. A method of preparing sucralose in which a sucrose octaacylate is treated with an enzyme or combination of enzymes capable of selectively removing acyl groups from the 4-, 1′- and 6′- positions to obtain the corresponding 2, 3, 6, 3′, 4′-penta-acylate, the pentaacylate is chlorinated and the chlorinated product is deacylated, said enzyme being selected from the group consisting of pancreatic lipases, yeast esterase, fungal α-amylase, subtilisins, Aspergillus melleus protease and α-galactosidases.

19. The method of claim 18 in which the enzyme or combination of enzymes comprises an enzyme selected from the group consisting of yeast esterase and subtilisin Carlsberg.

20. The method of claim 18 in which said sucrose octaacylate is prepared by treating sucrose octaacetate with an amine base to obtain the 2, 3, 4, 6, 1′, 6′-hexaacetate which is then butyrylated at the 3′- and 4′- positions.

21. The method of claim 1 in which the organic solvent is water miscible.

22. The method of claim 1 in which the organic solvent is slightly water miscible.

* * * * *